United States Patent [19]

Stevens et al.

[11] 3,932,262
[45] Jan. 13, 1976

[54] PORTABLE ELECTROPHORESIS APPARATUS USING MINIMUM ELECTROLYTE

[75] Inventors: Mario R. Stevens, Glendora; John Michael Vickers, La Canada, both of Calif.

[73] Assignee: California Institute of Technology, Pasadena, Calif.

[22] Filed: Oct. 15, 1973

[21] Appl. No.: 406,296

[52] U.S. Cl. .............................. 204/299; 204/180 S
[51] Int. Cl. .............................................. B01k 5/00
[58] Field of Search ............ 204/299, 180 S, 180 G

[56] References Cited
UNITED STATES PATENTS

| | | |
|---|---|---|
| 2,768,948 | 10/1956 | McDonald et al. ............... 204/180 S |
| 2,888,392 | 5/1959 | Grassmann et al. ............ 204/299 X |
| 3,326,795 | 6/1967 | Shandon ............................. 204/299 |
| 3,421,998 | 1/1969 | Yallen................................. 204/299 |
| 3,594,263 | 7/1971 | Dwyer et al. ...................... 204/299 |

Primary Examiner—Howard S. Williams
Assistant Examiner—A. C. Prescott

[57] ABSTRACT

An electrophoresis unit for use in conducting electrophoretic analysis of specimens is disclosed. The unit includes a sealable container in which a substrate mounted specimen is suspended in an electrolytic vapor. A heating unit is employed to heat a supply of electrolyte to produce the vapor. The substrate is suspended within the container by being attached between a pair of clips which also serve as electrodes to which a direct current power source may be connected.

12 Claims, 2 Drawing Figures

PORTABLE ELECTROPHORESIS APPARATUS USING MINIMUM ELECTROLYTE

BACKGROUND OF THE INVENTION

1. Origin of the Invention

The invention described herein was made in the performance of work under a NASA contract and is subject to the provisions of Section 305 of the National Aeronautics and Space Act of 1958, Public Law 85-568 (72 Stat. 435; 42 U.S.C. 2457).

2. Field of the Invention

The present invention is directed to an electrophoresis apparatus and more particularly to improvements in mounting an electrophoresis substrate to permit ionographic migration with a minimum of electrolyte.

3. Description of the Prior Art

Electrophoresis has been utilized in analytical procedures. For example, electrophoresis is used in the field of geology for the isolation of amino acids from soil, sedimentary rock, etc. Generally, a porous substrate member is moistened or impregnated with a buffer solution in the form of an electrically conductive fluid. The suitable prepared specimen is deposited upon the substrate and is subjected to an electric field such as may be provided by maintaining an electrical potential difference between two electrodes, to have the components of the specimen undergo an ionographic migration. Particular components of the specimen can be subsequently rendered visible by the use of dyes for purposes of identification.

Generally, each end of the porous substrate is maintained in contact with the electrolytic solution through the use of a wick or by direct immersion in the solution. Electrodes are immersed in the electrolytic solution to allow a desired voltage gradient to be maintained across the porous substrate when a direct current power source is attached to the electrodes. The central portion of the substrate receives the specimen to be analyzed and is generally maintained out of direct contact with either of two pools of electrolyte. This has been accomplished by providing a central support which serves the dual function of supporting the porous substrate and separating the electrolytic solutions. A common arrangement may involve a porous, flexible membrane sheet which is bent at opposite ends and dipped into the pools of electrolyte or which is supported on wicks that extend into the respective pools of electrolyte.

As noted in U.S. Pat. No. 3,715,295, one of the recurrent problems in electrophoresis has been the undesired evaporation of electrolytic liquid from the substrate which can result in a loss of effectiveness due to pH changes and changes in strength due to increased salt production in the electrolyte. Another problem is mentioned in U.S. Pat. No. 3,494,846 as being a difficulty in providing a acceptable electrical connection between the substrate and the electrolyte. Frequently, an undesirable potential drop will be developed at the site of the charged electrolyte-substrate interface. In addition, high resistance at the wick contact points and at the bent portions of the substrates may cause unwanted secondary electrolysis and/or cause heating which tends to evaporate the electrolyte liquid on the substrate. The secondary electrolysis tends to re-mix the specimen components and thus at least partially counteracts the desired electrophoresis separation.

Evaporation provides the additional problem of condensed vapors which form on the walls of a cell and run back into, and mix with, the electrolyte fluid to thereby create undesirable gradients of concentration. Prior art techniques such as disclosed by U.S. Pat. Nos. 3,047,489 and 3,317,417 have been used in an effort to eliminate the evaporation problem in electrophoresis cells. For example, cellular material such as sponges have been inserted within the electrophoresis cell to prevent vapor spaces.

One of the many uses of electrophoresis is in the field of analyzing blood serum proteins; for example, for the detection and diagnosis of sickle cell disease and other homoglobinopathies. Since a large segment of the population is subject to these diseases, it is necessary to develop an electrophoresis apparatus that eliminates or overcomes the problems of the prior art and is capable of a rapid and possibly automatic testing procedure. To understand the magnitude of the problem, it has been estimated that as many as 25 million persons may be subject to sickle cell disease of which as many as 2½ million could be carriers of the S trait and approximately fifty thousand people will suffer from the homozygous SS disease. In addition, many of these people can suffer from either a single or combined hemoglobinopathies of other types.

Presently, electrophoresis tests are conducted in the conventional manner; that is, the cell apparatus is divided into two sumps for containing two pools of liquid electrolyte between which a substrate of cellulose acetate is positioned to have opposite ends respectively submerged within a pool. Surface tension causes the substrate to become saturated. A voltage gradient is created across the substrate by placing in each pool one of two electrodes connected to a direct current power source. Preparing the cell apparatus for a test requires preparing approximately 1000 cc. of electrolyte, filling the two sumps with this liquid and determining that the surfaces of the pools are at the same level to prevent an undesired flow of electrolyte through the substrate material which will interfere with the flow of ions from the specimen. After each test, the remaining contaminated liquid must be disposed of and the apparatus thoroughly cleaned.

Thus, there is a need in the prior art to provide an electrophoresis unit that is accurate and adaptable to processing large numbers of specimens.

OBJECTS AND SUMMARY OF THE INVENTION

It is a primary object of the present invention to provide an electrophoresis apparatus that permits repetitive use with a minimum of difficulty.

It is another object of the present invention to provide an electrophoresis unit in which a substrate is suspended in a saturated vapor requiring use of a minimum of electrolyte.

It is a further object of the present invention to provide an electrophoresis apparatus in which direct electrical contact with a substrate is maintained.

It is yet another object of the present invention to provide an electrophoresis apparatus in which a liquid electrolyte is used to provide a saturated vapor.

It is yet a further object of the present invention to provide an electrophoresis unit that is portable and is capable of efficient usage to obtain accurate results.

Briefly described, the present invention involves a portable, electrophoresis unit.

More particularly, the subject invention includes a sealed container in which a saturated vapor form a heated electrolyte or subcomponent thereof is used. A porous substrate on which a specimen being tested is deposited is electrically connected between a pair of clip electrodes and thereby suspended in the saturated vapor. A direct current power source is connected between the clip electrodes. A heater is molded into the container bottom for heating the electrolyte liquid to provide the saturated vapor.

Further objects and the many attendant advantages of the invention may be best understood by reference to the following detailed description taken in conjunction with the accompanying drawings in which like reference symbols designate like parts throughout the figures thereof.

DESCRIPTION OF THE PREFERRED EMBODIMENT

Figure 1:
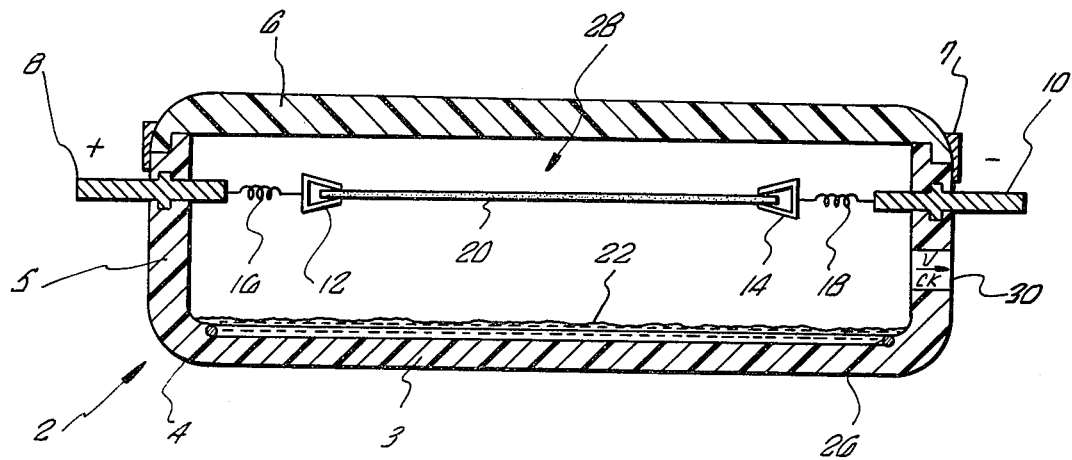
FIG. 1 is a cross-sectional side view of an electrophoresis unit in accordance with the present invention.

Referring to the drawings, an electrophoresis unit or electrophoretic cell 2 includes a container 4 having a bottom 3 and side walls 5 with a cover or lid 6. The container 4 and lid 6 can be sealed by the use of tape 7 or any other conventional sealing medium such as a gasket or the like. A pair of electrical plugs or electrodes 8 and 10, respectively, are mounted appropriately in the container side walls 5.

The plugs 8 and 10 are respectively connected to one of a pair of clip members 12 and 14 through the respective conductive springs 16 and 18. The electrode clip members 12 and 14 may be generally clad with platinum or some other relatively inert material to prevent chemical reaction with an electrolyte 22. The electrode clip members 12 and 14 are intended to be capable of clamping and supporting an electrophoresis substrate or porous membrane 20 therebetween.

The substrate 20 may be a micro-porous plastic sheet that is capable of being made transparent whereby the specimen subject to electrophoresis can be evaluated by light transmission scanning if desired. The substrate 20 will typically comprise a base member generally of plastic such as a polyester, polyamid or polycarbonate. Mylar, DuPont Corporation, No. 1000 D is an exemplary material that could be utilized as the base member. A porous material such as cellulose acetate or a mixture of cellulose nitrate and cellulose acetate may be mounted on the base member to form the desired micro-porous plastic sheet that is capable of transporting the electrolyte or buffer solution 22 by capillary action.

A heater 26 such as any known conventional resistance heater is preferably mounted in the container bottom 3. The heater 26 serves to heat the electrolyte 22 to produce and maintain a saturated vapor within the interior cavity 28 of the container 4. The temperature of the electrolyte 22 can be monitored, if desired, by a thermocouple and feedback circuit connected to the heater 26 (not shown) to maintain the saturated environment in the cavity 28. For purposes of the present invention, saturated vapor is intended to refer to the state in which the maximum amount of electrolyte, or sub-component thereof, is diffused in the air in a gaseous state and at which no more can be absorbed, dissolved or retained.

A pyridine-acetic acid-water solution having a pH of 5.2 and used for isolating amino-acids, is a typical electrolyte that is useable with the subject invention. It is to be understood that certain electrolytes that are available as a gel may also be used.

A pressure relief valve 30 may be provided on the side walls 5 as a safety device to prevent the formation of excess pressure within the container 4.

In operation, a technician would place a small quantity of electrolyte 22, for example 25 cc., in the container 4. A porous substrate 20, pre-wetted with the electrolyte 22, would then be mounted in the clip electrodes 12 and 14. Preferably, the length of the clip electrodes 12 and 14 is approximately equal to the width of the substrates 20 to have a uniform electric field across the length of the porous substrate 20. A specimen 32 would be deposited on the porous substrate 20. Taking sickle cell analysis as an illustrative example, a blood specimen 32, after appropriate centrifugal separation of the red cells and lysis with an aqueous saponin solution, could be applied to the porous substrate 20 as a drop or a very narrow band extending along the width of the substrate 20. The container 4 is then sealed with the tape or gasket 7 and the heater 26 is energized to produce the saturated vapor within the cavity 28. The amount of electrolyte used need only be enough to provide the saturated vapor since it is not utilized to provide electrical contact or source of liquid electrolyte for the substrate 20.

An acceptable voltage provided from a direct current power source would be in the neighborhood of 200 volts. Using 200 volts, approximately 0.6 miliamperes of current is conducted through the porous substrate 20. Tests that have been conducted reveal that hemoglobin migration concentrations, such as indicated by the reference numbers 34 and 36, that are obtained with the present invention are comparable to results that are obtainable by using other presently commercially available standard electrophoresis units.

Since the electrolyte 22 is not contaminated by the specimen 32, there is no necessity for cleansing the container 4 and removing the remaining electrolyte after each test procedure. Further, since the electrical contact to the porous substrate 20 is provided directly by the electrode clips 12 and 14, the difficulties presented by dilution or concentration gradients formed in liquid electrolyte pools are avoided.

Figure 2:
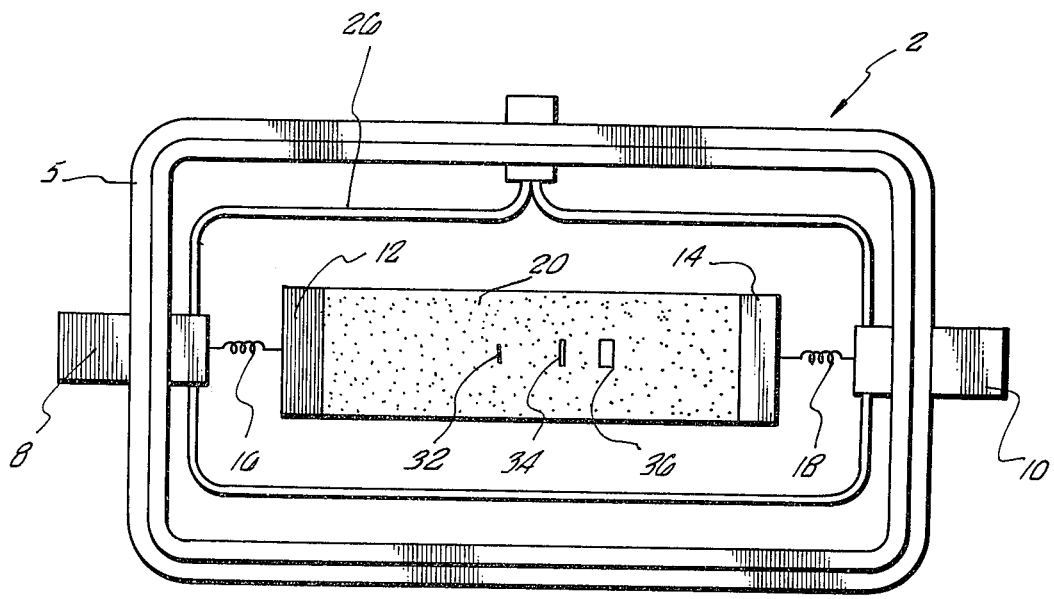
FIG. 2 is a plan view of an electrophoresis unit in accordance with the present invention.

While the foregoing description of the present invention concerns a preferred embodiment that has been developed to date, it is not intended to be limiting with respect to the broad principles involved herein. For example, the present invention could be applied to an automated system with a continual progression of specimens being subjected to a saturated environment. As with the specimen in FIGS. 1 and 2, subsequent staining and optical scanning with a densitometer could also be utilized for an automated procedure.

Various modifications of the present invention are possible. For example, the lid 6 could be connected to the electrical system of the electrical plugs 8 and 10 in such a manner to shut off the electrical power when the lid 6 is open as an operator safety feature. Further, the interior surface of the lid 6 can be designed to be slanted relative to the surface of substrate 20 when the lid 6 is in a closed position to prevent any condensate from dropping onto the substrate 20. It is to be noted that the invention described may be readily used outside a laboratory due to its portability. For example, blood samples can be taken and analyzed at the patients's bedside, in a doctors's office, or other suitable location.

It is to be understood that the supply of electrolyte maintained in the electrophoresis unit serves the primary purpose of countering evaporation of the electrolyte with which the substrate was impregnated. As is well known, water is the solvent in many electrolytic solutions and would be the substance that is evaporated. Accordingly, it follows that it would, in such cases, be possible to simply have a source of water rather than an electrolytic solution maintained in the unit to counter the evaporation of the water solvent on the substrate.

It is to be further understood that although the foregoing discussion has described the analysis of a blood specimen as an exemplary electrophoretic test procedure, the subject invention would be highly useful for the analysis of any other specimen that is an electrolyte or could be made an electrolyte by a pH adjustment. Accordingly, an analysis could be in the fields of geology, biology, archaeology, etc. and involve a wide range of different substances.

While a preferred embodiment of the present invention has been described hereinabove, it is intended that all matter contained in the above description and shown in the accompanying drawings be interpreted as illustrative and not in a limiting sense and that all modifications, constructions and arrangements which fall within the scope and spirit of the invention may be made.

What is claimed is:

1. An electrophoresis unit that is useable for conducting electrophoretic analyses of specimens mounted on substrates that have been saturated with an electrolyte, said electrophoresis unit comprising:
    a sealable container having an interior cavity defined by container walls;
    means for sustaining a saturated electrolytic vapor in said cavity of said container; and
    electrode means for suspending said substrate within said cavity of said container, said electrode means extending from outside said container through the walls thereof and including a pair of securing members for suspending said substrate therebetween and within said cavity, and a pair of terminal members respectively connected to said securing members for being connected to provide direct current power thereto.

2. The electrophoresis unit defined by claim 1 wherein the means for sustaining a saturated vapor includes:
    a supply of electrolyte situated within the cavity of said container; and
    means for heating said supply of electrolyte to produce said electrolytic vapor.

3. The electrophoretic unit defined by claim 1 wherein the substrate on which a specimen is mounted is maintained physically separated from said supply of electrolyte.

4. The electrophoresis unit defined by claim 1 wherein said pair of securing members are a pair of clips.

5. The electrophoresis unit defined by claim 1 wherein the electrode means further includes spring members for connecting said securing members to said terminal members.

6. The electrophoresis unit defined by claim 2 wherein said means for heating is molded into a bottom wall of said container.

7. The electrophoretic unit defined by claim 6 wherein the substrate on which a specimen is mounted in maintained physically separated from said supply of electrolyte.

8. The electrophoresis unit defined by claim 7 wherein the electrode means further includes spring members for connecting said securing members to said terminal members.

9. The electrophoresis unit defined by claim 8 wherein said pair of securing members are a pair of clips.

10. An electrophoretic cell that is useable for electrophoretic analysis of specimens applied to substrates that have been saturated with an electrolyte including a solvent, said electrophorectic cell comprising:
    a sealable container having walls defining an interior cavity;
    means for providing a saturated vapor of said solvent in said interior cavity of said container; and
    electrode means for allowing electrical current to be conducted through said substrate from a power source connected to said electrode means external to said interior cavity and for holding said substrate in said saturated vapor wherein said saturated vapor serve to counter evaporation of said solvent from said substrate.

11. The electrophoretic cell defined by claim 10, wherein said means for providing a saturated vapor includes:
    a supply of said solvent in said container; and
    means for heating said supply of said solvent.

12. The electrophoretic cell defined by claim 11, wherein said electrode means includes means for being attached to said substrate.

* * * * *